United States Patent
Eidamshaus et al.

(10) Patent No.: US 10,995,057 B2
(45) Date of Patent: May 4, 2021

(54) METHOD FOR HYDROGENATING NITRILES IN THE PRESENCE OF A RUTHENIUM CATALYST CARRIED ON $ZRO_2$

(71) Applicant: BASF SE, Ludwigshafen am Rhein (DE)

(72) Inventors: Christian Eidamshaus, Ludwigshafen (DE); Thomas Krug, Ludwigshafen (DE); Johann-Peter Melder, Ludwigshafen (DE); Joerg Pastre, Ludwigshafen (DE); Regine Helga Bebensee, Ludwigshafen (DE); Stephanie Jaegli, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/323,578

(22) PCT Filed: Sep. 1, 2017

(86) PCT No.: PCT/EP2017/071936
§ 371 (c)(1),
(2) Date: Feb. 6, 2019

(87) PCT Pub. No.: WO2018/046393
PCT Pub. Date: Mar. 15, 2018

(65) Prior Publication Data
US 2019/0169112 A1    Jun. 6, 2019

(30) Foreign Application Priority Data

Sep. 8, 2016  (EP) .................................... 16187732

(51) Int. Cl.
| | | |
|---|---|---|
| C07C 209/48 | (2006.01) | |
| C07C 213/02 | (2006.01) | |
| B01J 23/46 | (2006.01) | |
| B01J 21/06 | (2006.01) | |
| C07C 211/03 | (2006.01) | |
| C07C 211/14 | (2006.01) | |
| C07C 217/08 | (2006.01) | |

(52) U.S. Cl.
CPC .......... *C07C 209/48* (2013.01); *B01J 23/462* (2013.01); *C07C 213/02* (2013.01); *B01J 21/066* (2013.01); *C07C 211/03* (2013.01); *C07C 211/14* (2013.01); *C07C 217/08* (2013.01)

(58) Field of Classification Search
None
See application file for complete search history.

(56) References Cited

U.S. PATENT DOCUMENTS

2002/0158223 A1* 10/2002 Fukushima ........... C07C 213/02
                                                            252/8.63
2009/0281348 A1* 11/2009 Henkelmann ............ B01J 38/04
                                                            560/96

FOREIGN PATENT DOCUMENTS

| DE | 102 16 745 A1 | 10/2003 |
|---|---|---|
| EP | 0 363 843 A2 | 4/1990 |
| EP | 0 636 409 A1 | 2/1995 |
| EP | 2 684 862 A1 | 1/2014 |
| WO | WO 96/23802 A1 | 8/1996 |
| WO | WO 2015/086639 A2 | 6/2015 |

OTHER PUBLICATIONS

International Search Report dated Oct. 2, 2017 in PCT/EP2017/071936 filed Sep. 1, 2017.

Guangyin, F. et al., "Highly Efficient Hydrogenation of Methyl Propionate to Propanol over Hydrous Zirconia Supported Ruthenium," Chinese Journal of Chemistry, vol. 29, No. 2, Feb. 1, 2011, pp. 229-236, XP055121946.

* cited by examiner

*Primary Examiner* — Sudhakar Katakam
*Assistant Examiner* — Jennifer C Sawyer
(74) *Attorney, Agent, or Firm* — Grüneberg and Myers PLLC

(57) ABSTRACT

The present invention relates to a process for hydrogenating nitriles with hydrogen in the presence of a $ZrO_2$-supported ruthenium catalyst.

15 Claims, No Drawings

METHOD FOR HYDROGENATING NITRILES IN THE PRESENCE OF A RUTHENIUM CATALYST CARRIED ON ZRO₂

The present invention relates to a process for hydrogenating nitriles with hydrogen in the presence of a $ZrO_2$-supported ruthenium catalyst.

The hydrogenation of nitriles is the most important operation for preparing primary amines. Nitrile hydrogenations on the industrial scale are carried out typically over cobalt-containing fixed-bed catalysts or in the presence of suspension catalysts such as Raney nickel and Raney cobalt, and are known from the literature.

Only a few examples describe the hydrogenation of nitriles over ruthenium-containing catalysts.

C. Ortiz-Cervantes, I. Iyanez, J. J. Garcia et al. in J. Phys. Org. Chem. 2013, 25, 902-907 describe the deployment of ruthenium nanoparticles in the hydrogenation of acetonitrile, benzonitrile, and propionitrile.

WO96/23802 describes the hydrogenation in the presence of homogeneously dissolved Ru catalysts with phosphane ligands—for example, in the hydrogenation of adiponitrile.

An example of a supported ruthenium catalyst is described in EP-A 2684862. Described here is the batch hydrogenation of iminodiacetonitrile for the preparation of diethylenetriamine (DETA). A ruthenium catalyst supported on $Al_2O_3$ is used in this case. There is no description, however, of a ruthenium catalyst supported on $ZrO_2$.

The hydrogenation of nitriles is often carried out using fixed-bed Co catalysts, as described for example in Ullmann's Encyclopedia of Industrial Chemistry "Amines, Aliphatic", DOI: 10.1002/14356007.a2_001. Under the reaction conditions typical of hydrogenations, certain nitriles tend to release acrylonitrile or hydrocyanic acid. Such nitriles can typically be hydrogenated only with low space-time yields. Examples are N,N-biscyanoethylalkylamines, cyanoethylated alcohols, and alpha-aminonitriles.

The hydrogenation of such demanding nitriles in general takes place efficiently only over suspension catalysts. For example, the hydrogenation of N,N-biscyanoethylmethylamine over Raney metal catalysts is described in EP0363843 and by Mikolajewska et al., Acta Pol. Pharm., 1966.

There is no description of efficient fixed-bed catalysts which hydrogenate the aforesaid nitriles with good space-time yields.

The object of the present invention, therefore, is to provide a fixed-bed process for hydrogenation that allows not only the hydrogenation of nitriles in general with good space-time yields but which at the same time allows the hydrogenation even of demanding nitriles such as N,N-biscyanoethylalkylamines, cyanoethylated alcohols, and alpha-aminonitriles, for example, with space-time yields just as good as in the case of simple nitriles. In such a process, furthermore, the catalyst is to exhibit long-lasting high activity and to undergo deactivation only slowly.

This object is achieved by a process for hydrogenating nitriles in the presence of hydrogen and a fixed-bed ruthenium catalyst supported on $ZrO_2$.

The process of the invention is advantageous if the fixed-bed Ru catalyst used comprises 0.05 to 20 wt % of ruthenium, based on the total weight of the catalyst.

The process of the invention is advantageous if the nitrile hydrogenation process is operated continuously.

The process of the invention is advantageous if the nitriles for hydrogenation are dinitriles.

The process of the invention is advantageous if the nitriles for hydrogenation are selected from the group of cyanoethylated single and multiple alcohols, cyanoethylated amines, and alpha-aminonitriles.

The process of the invention is advantageous if the hydrogenation is carried out solventlessly.

The process of the invention is advantageous if hydrogenation is carried out at temperatures in the range from 20 to 200° C. and pressures in the range from 1 to 300 bar.

In the process of the invention it is possible to use any nitriles known to the skilled person. Preferred is the use of alpha-aminonitriles, cyanoethylated single and multiple amines, and cyanoethylated single and multiple alcohols. Particularly preferred is the use of aminoalkyl-alpha-aminonitriles, alkyl-alpha-aminonitriles, cyanoethylated amines, cyanoethylated diamines, cyanoethylated 1,2- and 1,3-diols, and cyanoethylated alkyl alcohols. Especially preferred is the use of aminoacetonitrile, imidodiacetonitrile, dimethylaminoacetonitrile, N,N-dimethylaminopropyl nitrile, biscyanoethyl glycol, 3-methoxypropylnitrile, 3-hydroxypropylnitrile, N,N-biscyanoethylethylenediamine, and N,N-biscyanoethylmethylamine. Very particularly preferred in particular is dimethylaminoacetonitrile, N,N-dimethylaminopropylnitrile, biscyanoethyldiethylene diglycol, N,N-biscyanoethylmethylamine.

The temperatures at which the hydrogenation is carried out are in a range from 20 to 200° C., preferably at 60 to 180° C., more preferably from 80 to 140° C., very preferably at 90 to 130° C.

The pressure prevailing during hydrogenation is generally at 1 to 300 bar, preferably at 20 to 300 bar, more preferably at 40 to 240 bar, very preferably at 80 to 200 bar.

In one preferred embodiment, the nitriles used are supplied at a hydrogenation rate which is not greater than the rate at which the nitriles react with hydrogen during the hydrogenation.

The supply rate is preferably to be set such that full conversion is achieved. This is influenced by temperature, pressure, nature of the nitrile compound, amount of catalyst, amount of reaction medium, quality of mixing of the reactor contents, residence time, etc.

The process of the invention is carried out in the presence of a ruthenium catalyst supported on $ZrO_2$. The Ru catalyst supported on $ZrO_2$ may in principle have any of the forms known to the skilled person for nitrile hydrogenation, such as strands, beads, tablets, extrudates, powders, chips.

Before being used, the Ru catalyst supported on $ZrO_2$ is activated outside the reactor or in the reactor by reduction of oxidized ruthenium species in a hydrogen-containing gas stream at elevated temperature. If the catalyst is reduced outside the reactor, passivation may take place thereafter by means of an oxygen-containing gas stream or embedment into an inert material, in order to prevent uncontrolled oxidation in air and to permit safe handling. Inert material used may comprise organic solvents such as alcohols or else water or an amine, preferably the reaction product.

The catalytically active mass of particularly preferred $ZrO_2$-supported ruthenium catalysts prior to the reduction with hydrogen is 0.05 to 20 wt %, preferably 0.05 to 15 wt %, of ruthenium, based on the total catalyst. These particularly preferred Ru catalysts supported on $ZrO_2$, and their preparation, are described in WO-A2 2015/086639 from page 7, lines 5 to 38. From page 5, line 40 to page 8, line 42, WO-A2 2015/086639 also describes the preferred physical properties of such $ZrO_2$-supported Ru catalysts in the form of fixed-bed catalysts.

The process of the invention may be carried out in the presence of a solvent or without solvent. Its implementation without solvent is preferred. If, however, it is operated in the presence of a solvent, solvents suitable in principle include all those known to the skilled person—the solvents must preferably behave inertly toward the nitriles that are to be used.

Possible solvents are organic solvents, examples being aromatic and aliphatic hydrocarbons, such as toluene, alcohols such as methanol, ethanol, propanol, isopropanol, butanol, isobutanol, secondary butanol, and tertiary butanol, amines, such as EDA and/or ethylamines and ammonia, and ethers, such as diisopropyl ether, diisobutyl ether, glycol dimethyl ether, diglycol dimethyl ether, dioxane, and tetrahydrofuran (THF), and amides such as N,N-dimethylacetamide and N,N-dimethylformamide.

The solvent is preferably an aromatic hydrocarbon, an alcohol, an amine, or an ether. Preferred in the process of the invention are cyclic ethers and amines. Particularly preferred are tetrahydrofuran and ammonia. Especially preferred is ammonia.

The nitrile is normally mixed with the solvent so as to set a nitrile content in the solution of 0.5 to 95 wt %. The concentration of the nitriles in the solution in which the hydrogenation is carried out ought to be selected such as to allow the establishment of a suitable supply rate and/or residence time. The nitrile is preferably mixed with the solvent in such a way as to set a nitrile content in the solution of 5 to 75 wt %.

The reaction of the nitriles with hydrogen in the presence of catalysts may be carried out in customary reaction vessels suitable for the catalysis, in a fixed bed, fluidized bed, continuously, semibatchwise, or batchwise. Reaction vessels suitable for implementing the hydrogenation are those which allow the nitriles and the catalyst to be contacted with the hydrogen under pressure.

The hydrogenation over the $ZrO_2$-supported fixed-bed Ru catalyst takes place preferably in one or more tube reactors or else tube bundle reactors.

The hydrogenation of the nitrile groups is accompanied by release of heat, which in general must be removed. Heat removal may be accomplished by incorporated heat transfer surfaces, cooling jackets, or external heat transfer means in a circulation system around the reactor. The hydrogenation reactor or a hydrogenation reactor cascade may be run in a straight-pass operation. An alternative option is a circulation regime, in which a portion of the discharge from the reactor is returned to the reactor entrance, preferably without prior work-up of the circulation stream.

In particular, the circulation stream may be cooled simply and inexpensively by means of an external heat transfer means, this being the way in which the heat of reaction is removed.

The reactor can also be operated adiabatically. In the case of adiabatic operation of the reactor, the temperature increase in the reaction mixture can be limited by cooling of the feeds or by supply of "cold" organic solvent.

Since in that case there is no need for the reactor itself to be cooled, a simple and inexpensive construction is possible. An alternative is a cooled tube bundle reactor.

Any organic solvents in the reaction discharge are generally separated off by distillation. The amines of the invention, in particular, can be isolated from the reaction product by methods known to the skilled person.

The invention is illustrated below using examples.

EXAMPLE 1

Continuous Hydrogenation of N,N-bis(cyanoethyl)methylamine (BCEMA) to N,N-bisaminopropylmethylamine (BAPMA) Over a Fixed-Bed Co and Ru Catalyst Pumped hourly through a vertical tube reactor (diameter: 0.5 cm, fill level 100 cm) operated at 170 bar and filled with 24.6 ml of a ruthenium catalyst (3 mm strands, described in WO-A2 2015/086639) or 20.8 ml of a cobalt catalyst (4 mm strands, described in EP636409) were 4.2 or 5.4 g of N,N-Bis(cyanoethyl)methylamine and 10.3-13.4 g of liquid ammonia (molar ratio 20). Passed through the reactor at the same time were 15-20 NL/h hydrogen.

After the reactor had been let down to atmospheric pressure, the hydrogenation discharge was analyzed by gas chromatography.

The temperature was selected so as to attain a conversion rate at the start of the experiment of approximately 99% (140° C. for the Co catalyst, 150° C. for the Ru catalyst).

|  | Run time [h] | Entry | Space velocity [$kg_{nitrile}/L_{cat.}$*h] | BAPMA [GC area %] | Bis-BAPMA [GC area %] | Sum of residual nitrile [GC area %] | Conversion [%] |
|---|---|---|---|---|---|---|---|
| Co cat. | 1 | 1 | 0.2 | 78.8 | 9.84 | 0.8 | 99.2 |
|  | 96 h | 2 | 0.2 | 73.4 | 8.4 | 6.1 | 93.9 |
| Ru cat. | 1 | 3 | 0.2 | 92.0 | 0.9 | 0.7 | 99.3 |
|  | 96 h | 4 | 0.2 | 91.3 | 1.1 | 0.8 | 99.2 |

The increase in the nitrile with the run time using the Co catalyst shows that under identical conditions, the ruthenium catalyst undergoes deactivation more slowly than the cobalt catalyst.

EXAMPLE 2

Batchwise Hydrogenation of 3-{2-[2-(2-cyanoethoxy)ethoxy]ethoxy}propanenitrile (Biscyanoethyldiethylene Diglycol) to 3-{2-[2-(3-aminopropoxy)ethoxy]ethoxy}propan-1-amine (TTD) Over a Co Catalyst and an Ru Catalyst A 270 ml autoclave with baffles and a disk stirrer was charged with 5.0 g of the appropriate catalyst (a cobalt catalyst in the form of 4 mm strands, described in EP636409, or a ruthenium catalyst in the form of 4 mm strands, described as in WO-A2 2015/086639) and 30 g of ammonia were injected. The autoclave is heated to 100° C. and hydrogen is injected up to a total pressure of 140 bar. The appropriate nitrile (6.0 g in 54 g of THF) was metered in over the course of 15 minutes. The reaction mixture was stirred under the reaction conditions for a further 60 minutes. The composition of the hydrogenation discharges obtained after letdown, determined by gas chromatography, are compiled in table 4.

| | TTD [GC area %] | Biscyanoethyl-diethylene glycol [GC area %] | |
|---|---|---|---|
| Co catalyst | 51.9 | 25.7 | Comparative example |
| 5% Ru/ZrO$_2$ | 72.8 | 7.03 | Inventive example |

EXAMPLE 3

Continuous Hydrogenation of 3-{2-[2-(2-cyanoethoxy)ethoxy]ethoxy}propanenitrile (Biscyanoethyldiethylene Diglycol) to 3-{2-[2-(3-aminopropoxy)ethoxy]ethoxy}propan-1-amine (TTD) Over a Fixed-Bed Ru Catalyst Pumped hourly through a vertical tube reactor (diameter: 0.5 cm, fill level 100 cm) filled with 37.2 ml of a ruthenium catalyst (3 mm strands) and operated at 170 bar were 13.5 g of 3-{2-[2-(2-cyanoethoxy)ethoxy]ethoxy}propanenitrile and 33.5 g of liquid ammonia (molar ratio 20). At the same time, 20 NL/h hydrogen were passed through the reactor.

After letdown to atmospheric pressure, the hydrogenation discharge was analyzed by gas chromatography.

The reaction was operated continuously over 960 hours without significant deactivation of the catalyst.

| | Propylamine | DEG | TTD | Biscyanoethyl-diethylene glycol | Others |
|---|---|---|---|---|---|
| 0 h | 0.3 | 0.8 | 80.2 | 0.3 | 18.4 |
| 960 h | 0.5 | 1.1 | 76.8 | 0.2 | 21.4 |

EXAMPLE 4

Comparison of the Al$_2$O$_3$ and ZrO$_2$ Supports in Semibatchwise Mode
Hydrogenation of N,N-dimethylaminopropionitrile (DMAPN) to N,N-dimethylaminopropylamine (DMAPA)

A 270 ml autoclave with baffles and a disk stirrer was charged with 5.0 g of the appropriate catalyst and 30 g of ammonia were injected. The autoclave is heated to 100° C. and hydrogen is injected up to a total pressure of 140 bar. The appropriate nitrile (6.0 g in 54 g of THF) was metered in over the course of 3 hours. The reaction mixture was stirred under the reaction conditions for a further 60 minutes. The composition of the hydrogenation discharges obtained after letdown, determined by gas chromatography, are compiled in tables 2 and 3.

| | DMAPA [GC area %] | DMAPN [GC area %] | |
|---|---|---|---|
| 2% Ru@Al$_2$O$_3$ | 73.6 | 24.9 | Comparative example |
| 2% Ru@ZrO$_2$ | 95.7 | 0.4 | Inventive example |

Hydrogenation of N,N-biscyanoethylmethylamine to N,N-bisaminopropylmethylamine
Analogous to the Hydrogenation of Dimethylaminopropionitrile

| | BAPMA [GC area %] | BCEMA [GC area %] | Mononitrile [GC area %] | |
|---|---|---|---|---|
| 2% Ru@Al$_2$O$_3$ | 42.6 | 31.7 | 22.2 | Comparative example |
| 2% Ru@ZrO$_2$ | 73.4 | 12.7 | 9.4 | Inventive example |

EXAMPLE 5

Comparison of the Supports Carbon and ZrO$_2$ in Semibatchwise Mode
Inventive Example: Hydrogenation of N,N-dimethylaminoacetonitrile (DMAAN) to N,N-dimethylaminoethylamine (DMAEA) Over Ruthenium on ZrO$_2$ A 270 ml autoclave with baffles and a disk stirrer was charged with 5.0 g of the catalyst (2% Ru on ZrO$_2$, 3 mm strands) and 40 ml of ammonia were injected. The autoclave is heated to 100° C. and hydrogen is injected up to a total pressure of 140 bar. DMAAN (6 g in 54 g of THF) was metered in over the course of 1.5 hours. The reaction mixture was stirred under the reaction conditions for a further 60 minutes. The composition of the hydrogenation discharges obtained after letdown, determined by gas chromatography, are compiled in table 5.

Comparative Example: Hydrogenation of N,N-dimethylaminoacetonitrile (DMAAN) to N,N-dimethylaminoethylamine (DMAEA) Over Ruthenium on Carbon A 270 ml autoclave with baffles and a disk stirrer was charged with 5.0 g of the catalyst (5% Ru on carbon) and 30 g of ammonia were injected. The autoclave is heated to 100° C. and hydrogen is injected up to a total pressure of 140 bar. DMAAN (6 g in 54 g of THF) was metered in over the course of 1.5 hours. The reaction mixture was stirred under the reaction conditions for a further 60 minutes. The composition of the hydrogenation discharges obtained after letdown, determined by gas chromatography, are compiled in table 5.

| | DMAEA [GC area %] | DMAAN [GC area %] | |
|---|---|---|---|
| 2% Ru@ZrO$_2$ | 94 | 0 | Inventive example |
| 5% Ru@C | 1 | 90 | Comparative example |

The invention claimed is:

1. A process, comprising hydrogenating at least one nitrile compound in the presence of hydrogen and a fixed-bed ruthenium catalyst supported on ZrO$_2$, wherein the fixed-bed ruthenium catalyst comprises 0.05 to 20 wt % of ruthenium, based on the total weight of the fixed-bed ruthenium catalyst.

2. The process according to claim 1, wherein the process is operated continuously.

3. The process according to claim 1, wherein the at least one nitrile compound comprises a dinitrile compound.

4. The process according to claim 1, wherein the nitrile compound is selected from the group consisting of a cyanoethylated single alcohol, a cyanoethylated multiple alcohol, a cyanoethylated amine and an alpha-aminonnitrile.

5. The process according to claim 1, wherein the hydrogenating does not occur in the presence of an added solvent.

6. The process according to claim 1, wherein the hydrogenating occurs in the presence of ammonia.

7. The process according to claim 1, wherein hydrogenation takes place at a temperature in the range from 20 to 200° C. and a pressure in the range from 20 to 300 bar.

8. The process according to claim 7, wherein the process is operated continuously.

9. The process according to claim 8, wherein the at least one nitrile compound comprises a dinitrile compound.

10. The process according to claim 9, wherein the nitrile compound is selected from the group consisting of a cyanoethylated single alcohol, a cyanoethylated multiple alcohol, a cyanoethylated amine and an alpha-aminonnitrile.

11. The process according to claim 10, wherein the hydrogenating does not occur in the presence of an added solvent.

12. The process according to claim 11, wherein the hydrogenating occurs in the presence of ammonia.

13. The process according to claim 1, wherein the fixed-bed ruthenium catalyst comprises 0.05 to 15 wt % of ruthenium, based on the total weight of the fixed-bed ruthenium catalyst.

14. The process according to claim 1, wherein the at least one nitrile compound comprises a dinitrile compound, wherein the hydrogenating does not occur in the presence of an added solvent, wherein the hydrogenating occurs in the presence of ammonia, and wherein the fixed-bed ruthenium catalyst comprises 0.05 to 15 wt % of ruthenium, based on the total weight of the fixed-bed ruthenium catalyst.

15. The process according to claim 1, wherein the fixed-bed ruthenium catalyst supported on $ZrO_2$ does not undergo significant deactivation when used continuously over 960 hours compared to a fixed-bed cobalt catalyst or a fixed-bed ruthenium catalyst supported on $Al_2O_3$.

\* \* \* \* \*